(12) United States Patent
Bernal et al.

(10) Patent No.: US 8,792,969 B2
(45) Date of Patent: Jul. 29, 2014

(54) RESPIRATORY FUNCTION ESTIMATION FROM A 2D MONOCULAR VIDEO

(71) Applicant: Xerox Corporation, Norwalk, CT (US)

(72) Inventors: Edgar A. Bernal, Webster, NY (US); Lalit Keshav Mestha, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 39 days.

(21) Appl. No.: 13/680,838

(22) Filed: Nov. 19, 2012

(65) Prior Publication Data

US 2014/0142435 A1    May 22, 2014

(51) Int. Cl.
*A61B 6/00*         (2006.01)

(52) U.S. Cl.
USPC ......................................................... 600/476

(58) Field of Classification Search
USPC ................................................. 600/473–480
See application file for complete search history.

(56) References Cited

U.S. PATENT DOCUMENTS

| | | | |
|---|---|---|---|
| 8,358,818 B2 * | 1/2013 | Miga et al. ..................... | 382/128 |
| 2008/0123927 A1 * | 5/2008 | Miga et al. ..................... | 382/131 |
| 2008/0146911 A1 | 6/2008 | Miyake | |
| 2008/0243142 A1 * | 10/2008 | Gildenberg .................... | 606/130 |
| 2009/0141124 A1 * | 6/2009 | Liu et al. ........................ | 348/65 |
| 2010/0249630 A1 | 9/2010 | Droitcour et al. | |
| 2011/0144517 A1 * | 6/2011 | Cervantes ...................... | 600/538 |
| 2012/0289850 A1 * | 11/2012 | Xu et al. ........................ | 600/529 |
| 2013/0035599 A1 * | 2/2013 | De Bruijn et al. ............. | 600/476 |
| 2013/0063434 A1 * | 3/2013 | Miga et al. ..................... | 345/420 |

OTHER PUBLICATIONS

Bernal et al., "Processing a Video for Tidal Chest Volume Estimation", U.S. Appl. No. 13/486,637, filed Jun. 1, 2012.
Bernal et al., "Minute Ventilation Estimation Based on Depth Maps", U.S. Appl. No. 13/486,682, filed Jun. 1, 2012.
Bernal et al., "Minute Ventilation Estimation Based on Chest Volume", U.S. Appl. No. 13/486,715, filed Jun. 1, 2012.
Bernal et al., "Processing a Video for Respiration Rate Estimation", U.S. Appl. No. 13/529,648, filed Jun. 21, 2012.
Mestha et al., "Filtering Source Video Data Via Independent Component Selection", U.S. Appl. No. 13/281,975, filed Nov. 8, 2011.
Mestha et al., "Removing Environment Factors From Video Signals Captured for Biomedical Measurements", U.S. Appl. No. 13/401,207, filed Feb. 21, 2012.

(Continued)

*Primary Examiner* — Sanjay Cattungal
(74) *Attorney, Agent, or Firm* — Philip E. Blair; Fleit Gibbons Gutman Bongini & Bianco P.L.

(57) ABSTRACT

What is disclosed is a system and method for processing a video acquired using a 2D monocular video camera system to assess respiratory function of a subject of interest. In various embodiments hereof, respiration-related video signals are obtained from a temporal sequence of 3D surface maps that have been reconstructed based on an amount of distortion detected in a pattern placed over the subject's thoracic region (chest area) during video acquisition relative to known spatial characteristics of an undistorted reference pattern. Volume data and frequency information are obtained from the processed video signals to estimate chest volume and respiration rate. Other respiratory function estimations of the subject in the video can also be derived. The obtained estimations are communicated to a medical professional for assessment. The teachings hereof find their uses in settings where it is desirable to assess patient respiratory function in a non-contact, remote sensing environment.

21 Claims, 9 Drawing Sheets

(56) References Cited

OTHER PUBLICATIONS

Mestha et al., "Video-based Estimation of Heart Rate Variability", U.S. Appl. No. 13/532,057, filed Jun. 25, 2012.

Xu et al., "Enabling Hybrid Video Capture of a Scene Illuminated With Unstructured and Structured Illumination Sources", U.S. Appl. No. 13/533,605, filed Jun. 26, 2012.

Xu et al., "Monitoring Respiration With a Thermal Imaging System", U.S. Appl. No. 13/103,406, filed May 9, 2011.

Perriollat et al., "Monocular Template-Based Reconstruction of Inextensible Surfaces", International Journal of Computer Vision (IJCV), vol. 95, No. 2, 2011, pp. 124-137.

Moreno-Noguer et al., "Capturing 3D Stretchable Surfaces From Single Images in Closed Form", IEEE Proceedings of the Conference on Computer Vision and Pattern Recognition (CVPR09), 2009, pp. 1842-1849.

Tarvainen et al., "An Advanced De-Trending Method With Application to HRV Analysis", IEEE Trans. Biomed. Eng., vol. 49, No. 2, pp. 172-175, Feb. 2002.

Salzmann et al., "Deformable Surface 3D Reconstruction From Monocular Images".

Jin et al., "Detection of Respiratory Rhythm From Photoplethysmography Signal Using Morphological Operators", IEEE, 2009, pp. 1-4.

Lowe, David G., "Distinctive Image Features From Scale-Invariant Keypoints", International Journal of Computer Vision 60(20), 2004, pp. 91-110.

Pilet et al., "Fast Non-Rigid Surface Detection, Registration and Realistic Augmentation", International Journal of Computer Vision, 2006.

Fischler et al., "Random Sample Consensus: A Paradigm for Model Fitting With Applications to Image Analysis and Automated Cartography", Communications of the ACM, vol. 24, No. 6, Jun. 1981, pp. 381-395.

Salzmann et al., "Reconstructing Sharply Folding Surfaces: A Convex Formulation".

Aoki et al., "Study on Respiration Monitoring Method Using Near-Infrared Multiple Slit-Lights Projection".

\* cited by examiner

RESPIRATORY FUNCTION ESTIMATION FROM A 2D MONOCULAR VIDEO

TECHNICAL FIELD

The present invention is directed to systems and methods utilizing a 2D monocular video acquisition system to capture video of a subject of interest being monitored for respiratory function assessment, and processing the video to obtain respiratory function measurements for that subject in a non-contact, remote sensing environment.

BACKGROUND

Monitoring respiratory events is of clinical importance in the early detection of potentially fatal respiratory events such as acute respiratory failure and pulmonary disease. Current technologies require that the resting patient wear sensing devices across their chest so that respiratory measurements can be estimated. Such a requirement can lead to discomfort, psychological dependence, and loss of dignity. Elderly patients and those suffering from chronic conditions are even more likely to suffer from such negative effects of monitoring. Moreover, wires with sensors are subject to device failure. Non-contact systems which can assess patient respiration function from video have arisen in this art. However, previous systems require expensive multi-modular 3D imaging systems which may be cost-prohibitive, particularly in developing countries. Systems and methods are needed which can enable respiratory function analysis without the need for expensive camera systems. However, derivation of volumetric data from 2D video signals acquired using an inexpensive 2D monocular video camera is a challenging problem to which the teachings hereof are particularly directed.

Accordingly, what is needed is a system and method for processing a video acquired using an inexpensive 2D monocular video acquisition system to assess respiratory function of a subject of interest.

INCORPORATED REFERENCES

The following U.S. Patents, U.S. Patent Applications, and Publications are incorporated herein in their entirety by reference.

"Processing A Video For Tidal Chest Volume Estimation", U.S. patent application Ser. No. 13/486,637, by Bernal et al. which discloses a system and method for estimating tidal chest volume by analyzing distortions in reflections of structured illumination patterns captured in a video of a thoracic region of a subject of interest being monitored for respiratory function.

"Minute Ventilation Estimation Based On Depth Maps", U.S. patent application Ser. No. 13/486,682, by Bernal et al. which discloses a system and method for estimating minute ventilation based on depth maps by analyzing distortions in reflections of structured illumination patterns captured in a video of a patient's chest area.

"Minute Ventilation Estimation Based On Chest Volume", U.S. patent application Ser. No. 13/486,715, by Bernal et al. which discloses a system and method for estimating minute ventilation based on chest volume by analyzing distortions in reflections of structured illumination patterns captured in a video of a thoracic region of a subject of interest being monitored for respiratory function.

"Processing A Video For Respiration Rate Estimation", U.S. patent application Ser. No. 13/529,648, by Bernal et al. which discloses a system and method for estimating a respiration rate for a subject of interest captured in a video containing a view of that subject's thoracic region.

"Filtering Source Video Data Via Independent Component Selection", U.S. patent application Ser. No. 13/281,975, by Mestha et al. which discloses a system and method for reconstructing a video signal such that selected signal components have been emphasized.

"Removing Environment Factors From Signals Generated From Video Images Captured For Biomedical Measurements", U.S. patent application Ser. No. 13/401,207, by Mestha et al. which discloses a system and method for removing undesirable periodic signals and random background noise from signals generated from video images captured from a RGB or infrared (IR) camera for improved accuracy and reliability of biomedical measurements.

"Video-based Estimation of Heart Rate Variability", U.S. patent application Ser. No. 13/532,057, by Mestha et al. which discloses a video-based system and method for estimating heart rate variability from time-series signals generated from video images captured of a subject of interest being monitored for cardiac function.

"Enabling Hybrid Video Capture of a Scene Illuminated with Unstructured and Structured Illumination Sources", U.S. patent application Ser. No. 13/533,605, by Xu et al. which discloses a system for enabling hybrid video capture of a scene being illuminated with structured and unstructured illumination sources.

"Monitoring Respiration with a Thermal Imaging System", U.S. patent application Ser. No. 13/103,406, by Xu et al. which discloses a thermal imaging system and method capable of capturing a video sequence of a subject of interest, and processing the captured image sequence on a frame-by-frame basis such that the subject's respiratory function can be continuously monitored without disturbing or disrupting the resting respiratory patient.

"Monocular Template-Based Reconstruction of Inextensible Surfaces", Mathieu Perriollat, Richard Hartley, and Adrien Bartoli, International Journal of Computer Vision (IJCV), Vol. 95, No. 2, pp. 124-137, (2011), which reviews two main classes of techniques, i.e., template-based methods that rely on establishing correspondences with a reference image in which the shape is already known, and non-rigid structure-from-motion techniques that exploit points tracked across the sequences to reconstruct a completely unknown shape.

"Capturing 3D Stretchable Surfaces From Single Images In Closed Form", Francesc Moreno-Noguer, Mathieu Salzmann, Vincent Lepetit, and Pascal Fua, IEEE Proceedings of the Conference on Computer Vision and Pattern Recognition, (CVPR09) pp. 1842-1849 (2009), which discloses a closed-form solution to 3D shape recovery of stretchable surfaces from point correspondences between an input image and a reference configuration.

"An Advanced De-Trending Method With Application To HRV Analysis", M. P. Tarvainen, P. O. Ranta-Aho, and P. A. Karjalainen, IEEE Trans. Biomed. Eng., Vol. 49, No. 2, pp. 172-175, (February 2002).

"Respiratory Physiology: The Essentials", John B. West, Lippincott Williams & Wilkins; $9^{th}$ Ed. (2011), ISBN-13: 978-1609136406.

BRIEF SUMMARY

What is disclosed is a system and method for processing a video acquired using a 2D monocular video acquisition system to assess respiratory function of a subject of interest. Respiration-related signals are obtained from a temporal sequence of 3D surface maps that have been reconstructed based on a characterization of an amount of distortion detected in a pattern placed over the subject's thoracic region (chest area) during video acquisition relative to known spatial characteristics of an undistorted reference pattern. Volume data and frequency information are obtained from the processed video signals to estimate chest volume and respiration rate. Other respiratory function estimations of the subject in the video can also be derived. The teachings hereof find their uses in settings where it is desirable to assess patient respiratory function in a non-contact, remote sensing environment.

One embodiment of the present method for image-based assessment of a respiratory function from an image or a video of a subject of interest acquired using a 2D monocular video camera. The embodiment wherein a subject's respiratory function is assessed from a video involves the following. First, a video of a target region of a subject of interest being monitored for respiratory function assessment is received. The target region can be, for instance, the subject's anterior thoracic region, a region of the subject's dorsal body, and/or a side view containing the subject's thoracic region. The video has been captured using a 2D monocular video acquisition system. The target region has a detectable pattern thereon with the pattern being either reflective or emissive in a given wavelength which is detectable by sensor elements in a detector array of the camera during acquisition of the video. The detectable pattern can be a pattern of reflective or emissive marks or having salient textural features imprinted on clothing worn over the target region. In other embodiments, the detectable pattern is salient textural characteristics on the target region itself. Once the video of the subject has been acquired, image frames of the video are processed to construct a temporal sequence of depth maps of the subject's target region by characterizing an amount of spatial distortion detected in the pattern over time relative to spatial characteristics of an undistorted reference pattern. The 3D depth maps are used to estimate various respiratory functions such as, for instance, tidal chest volume, minute ventilation, respiration rate, to name a few. The estimated respiratory functions are then used by medical professionals to monitor the subject for the occurrence of potentially fatal events such as PUHD-I, PUHD-II, SIDS, Respiratory Failure, and Pulmonary Disease.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for processing a video captured using an inexpensive 2D monocular video acquisition system to assess respiratory function of a subject of interest.

Non-Limiting Definitions

A "subject of interest", as used herein, refers to a patient being monitored for respiratory function assessment in accordance with the teachings hereof. Although the term "human", "person", or "patient" may be used throughout this text, the subject of interest may be something other than a human such as an animal. Therefore, use of "person" or "patient" is not to be viewed as limiting the scope of the appended claims solely to human beings.

Figure 1:
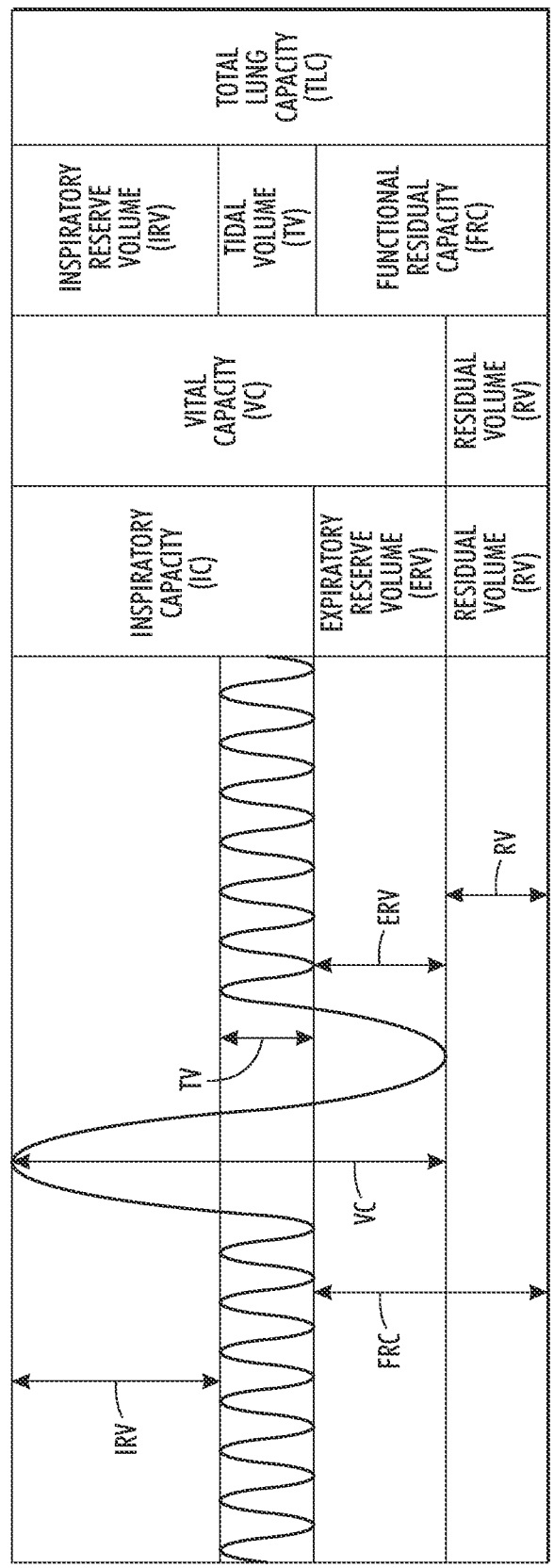
FIG. 1 graphically illustrates pulmonary volumes and capacities in an adult male.

The "respiratory function" is the function of anatomical portion of an organism that introduces gases into the interior of the organism, performs gas exchange, and expels waste gases out into the environment. In humans, carbon dioxide is one of the mediators of auto-regulation of blood supply, i.e., if $CO_2$ levels are high, capillaries around tissue expand to allow a greater blood flow to that tissue. Respiratory centers seek to maintain a safe arterial $CO_2$ pressure. FIG. 1 graphically illustrates pulmonary volumes and capacities in an adult male.

"Tidal chest volume" or simply "tidal volume" (TV) is the volume of air drawn into the lungs during tidal breathing. In a healthy, young adult, tidal chest volume is about 0.5 Liters of air. Since total lung capacity of an average adult human is approximately 6.0 liters of air, the lungs displace a relatively small volume after inspiration and expiration while tidal breathing. Restrictive pulmonary diseases such as pulmonary fibrosis, pneumothorax, Infant Respiratory Distress Syndrome, and the like, decrease lung volume, whereas obstructive pulmonary diseases such as asthma, bronchitis, and emphysema, obstruct airflow.

"Expiratory Reserve Volume" (ERV) is the maximal volume of air that can be exhaled from the end-expiratory position. In a healthy adult male, ERV is about 1.0 liter.

"Residual Volume" (RV) is the volume of air remaining in the lungs after maximal exhalation (residual air remains in the lungs no matter how hard one tries to expel all their air). In a healthy adult male, RV is about 1.2 liters.

"Inspiratory Reserve Volume" (IRV) is the maximal volume of air that can be inhaled at the end-inspiratory level. In a healthy adult male, IRV is about 3.3 liters.

"Vital Capacity" (VC) is the maximum amount of air a person can expel from the lungs after maximum inhalation. It is the sum of IRV, TV and ERV. In a healthy adult male, VC is about 4.6 liters.

"Inspiratory Capacity" (IC) is the volume of air that can be inhaled after normal inspiration. It is the sum of IRV and TV. In a healthy adult male, IC is about 3.8 liters.

"Functional Residual Capacity" (FRC) is the volume in the lungs at the end-expiratory position. It is the sum of ERV and RV. In a healthy adult male, FRC is about 2.2 liters.

"Total Lung Capacity" (TLC) is the total volume of air in the lungs at maximal inspiration. It is the sum of IRV, TV, ERV and RV. In a healthy adult male, TLC is about 6.0 liters.

"Respiration rate" is the number of breaths a subject takes in a certain amount of time typically in breaths per minute (bpm). During physical exertion when the body requires oxygenation at an increased rate, the respiration rate increases. Respiration rates may increase without physical activity due to fever, for example, or other medical conditions.

"Respiratory minute volume" or "minute ventilation" is the amount of air exchanged by the lungs in one minute. It can also refer to the amount of air inhaled in one minute (inhaled minute volume) or the amount of air exhaled in one minute (exhaled minute volume). Although the name implies a volume, minute ventilation is actually a flow because it represents a volume change over time. Respiratory minute volume is an important parameter in respiratory medicine due to its relationship with blood carbon dioxide levels.

A "2D monocular video" or simply "video", as is generally understood, is a time-varying sequence of image frames captured using a 2D monocular video acquisition system. The video may also contain other components such as, audio, time signals, and the like. The video may be processed or pre-processed to compensate for non-uniform illumination, motion induced blur, imaging blur, and slow illuminant variation.

A "2D monocular video acquisition system" refers to any standard RGB, black/white (B/W), or near-infrared (NIR) video camera that captures reflected or emitted energy from a target region of a subject of interest. Video acquisition systems have a 2D detector array with sensors which are sensitive to wavelengths reflected or emitted from a pattern detected on a target region of the subject during acquisition of the video. A video acquisition system has a plurality of outputs for outputting data on a per-channel basis and may further incorporate a processor for executing machine readable program instructions and a storage device such as a memory. Controllers may be provided to manipulate various illumination sources. A video acquisition system may further incorporate hardware executing machine readable program instructions for analyzing video to assess respiratory function in real-time using, in whole or in part, a software application working alone or in conjunction with one or more hardware resources.

"Receiving a video" is intended to be widely construed and means to retrieve, receive, capture with a video camera, or otherwise obtain a video for processing in accordance with the present method. The video can be retrieved from a memory or storage media internal to the video camera, or obtained from a remote device over a network. The video may also be retrieved from a media such as a CDROM, DVD or USB Drive. The video may be downloaded from a website for processing on a handheld cellular device or a handheld computing device such as an iPad.

A "target region" refers to a thoracic region (chest area) of a subject of interest whereon a pattern resides such that a video can capture an amount of distortion of that pattern to derive respiration-related video signals to assess respiratory function.

Figure 2:
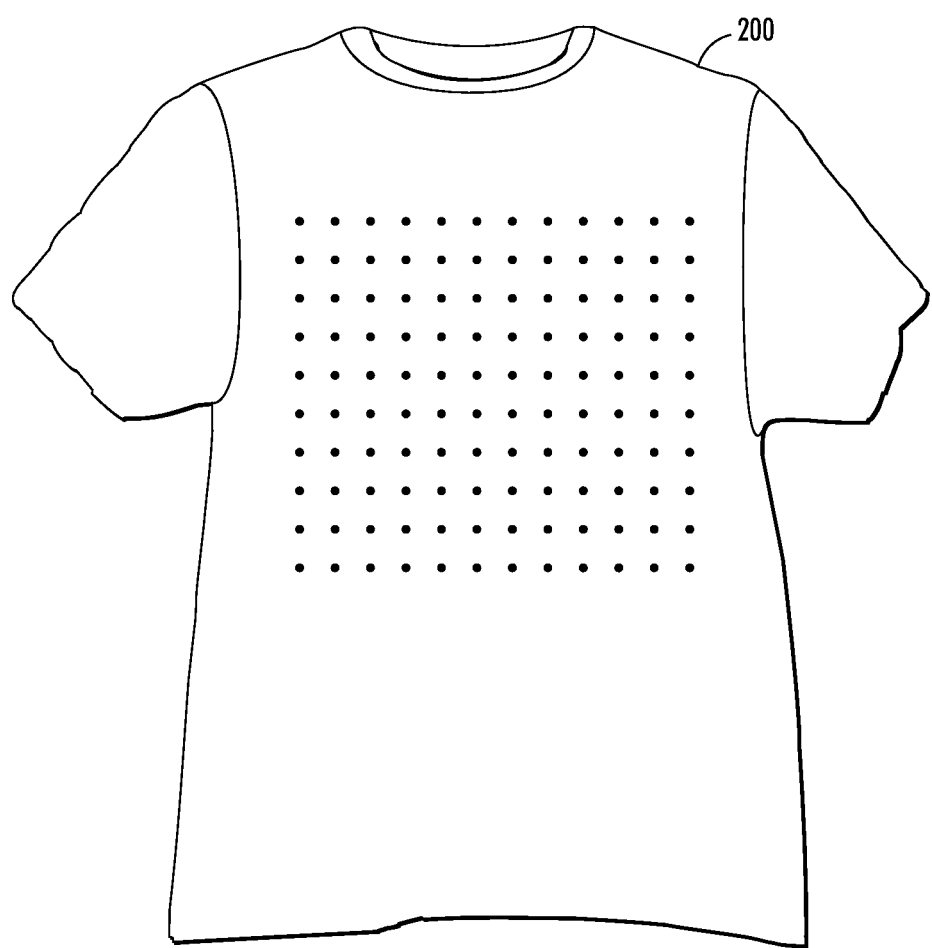
FIG. 2 illustrates a shirt 200 imprinted with a uniform pattern of reflective dots worn by a subject of interest over a target region.
Figure 3:
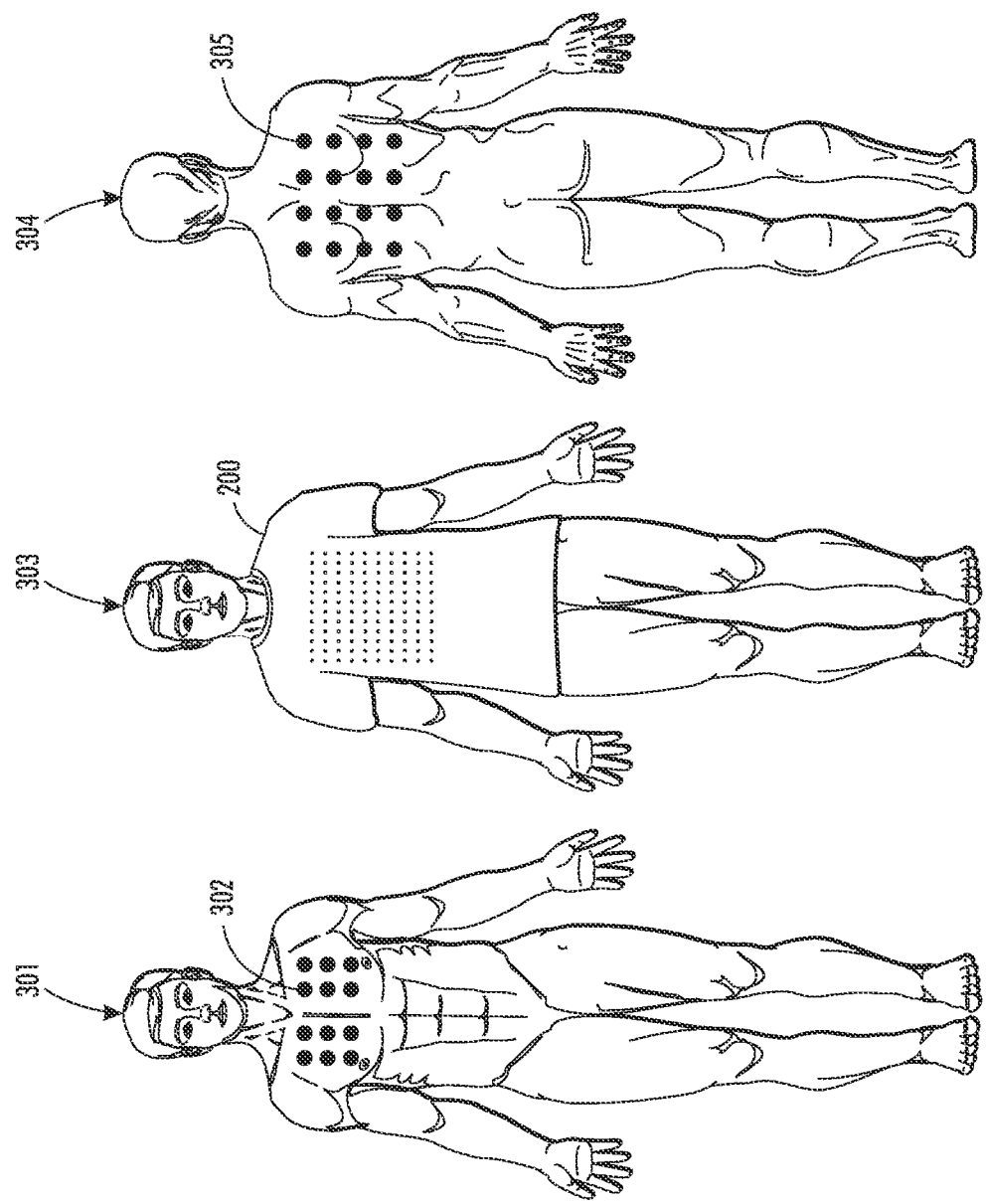
FIG. 3 shows subject of interest 301 having a plurality of reflective marks arrayed in a uniform grid on their front (anterior) thoracic region, subject 303 is shown wearing the shirt of FIG. 2, and subject 304 has similar dot marks on the posterior (back) thoracic region. It is to be noted that dot patterns can also be created using plurality of emitters such as LEDs in both anterior or posterior thoracic regions to cover regions fully or partially.

A "detectable pattern" refers to a pattern that emits or reflects a wavelength range that is detectable by sensors in the video camera's detector array. The pattern can be any reflective or emissive marks whether imprinted or otherwise affixed to clothing worn by the subject over the target region or which comprises textural characteristic present on the target region such as skin blemishes, scars, and even scales (in the case of a reptile), and the like. An example detectable pattern is shown in FIG. 2 which illustrates a shirt 200 imprinted with a uniform pattern of reflective dots in 12×10 grid with a 1 inch dot pitch along a horizontal and a vertical direction. The shirt would be worn by the subject. The reflective marks may be dots of reflective tape, reflective buttons, reflective fabric, or the like. The pattern may comprise emissive marks such as, for example, LED illuminators that have been sewn or otherwise affixed to the shirt. The pattern may be a uniform grid (as shown in FIG. 2), a non-uniform grid, a textured pattern, or a pseudo-random pattern so long as the pattern's spatial characteristics are known apriori. The spatial distortions of the detectable pattern caused by a movement of the subject's chest during respiration are compared to that of a reference pattern. FIG. 3 shows a subject of interest 301 having a plurality of reflective marks 302 arrayed in a uniform grid over a frontal region of their chest cage. Subject 303 is shown wearing shirt 200 of FIG. 2. Subject 304 is shown having a dot pattern comprising a plurality of emissive LEDs arrayed in a detectable pattern on their back.

Figure 4:
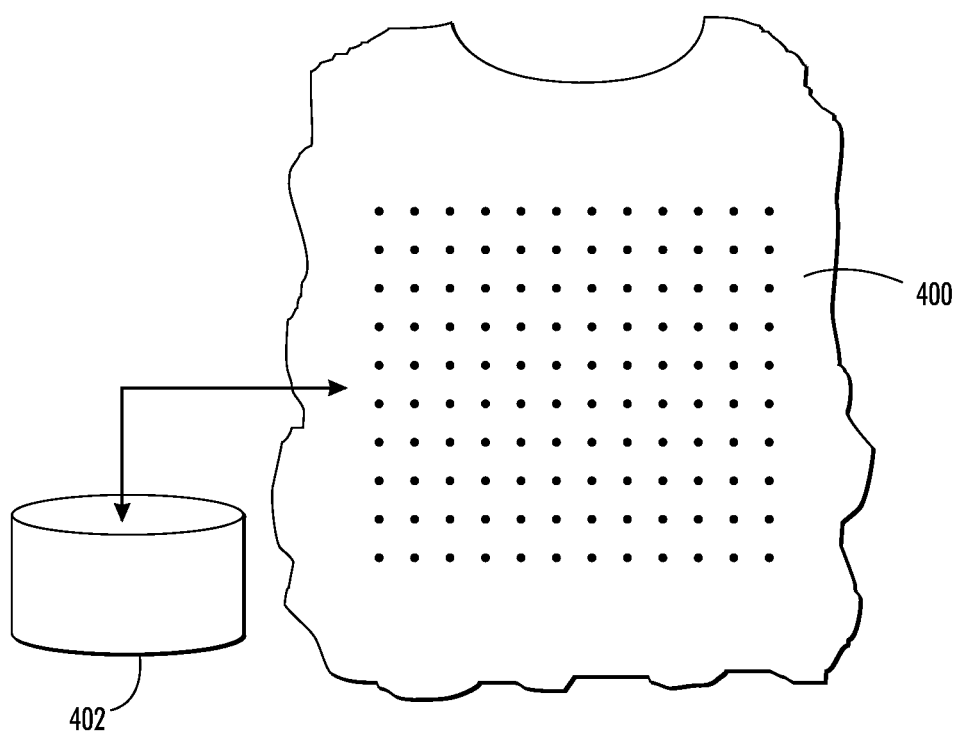
FIG. 4 shows a digital reference pattern comprising the same uniform grid of marks as shown on the shirt FIG. 2.

A "reference pattern" refers to an undistorted pattern having known spatial characteristics. The reference pattern may be a pattern on a physical object or may comprise a virtual pattern that exists in a digital space. FIG. 4 show a reference pattern 400 comprising a uniform grid of marks having defined spatial characteristics. The reference pattern is shown having been retrieved from storage device 402.

A "remote sensing environment" refers to the non-contact, unobtrusive, non-invasive acquisition of video signals of a subject of interest. The video device can be any distance away from the subject, for example, as close as less than an inch to as far as miles in the case of telemedicine. The teachings hereof advantageously find their uses in a remote sensing environment such that the respiratory patient is undisturbed.

Example Video Acquisition System

Figure 5:
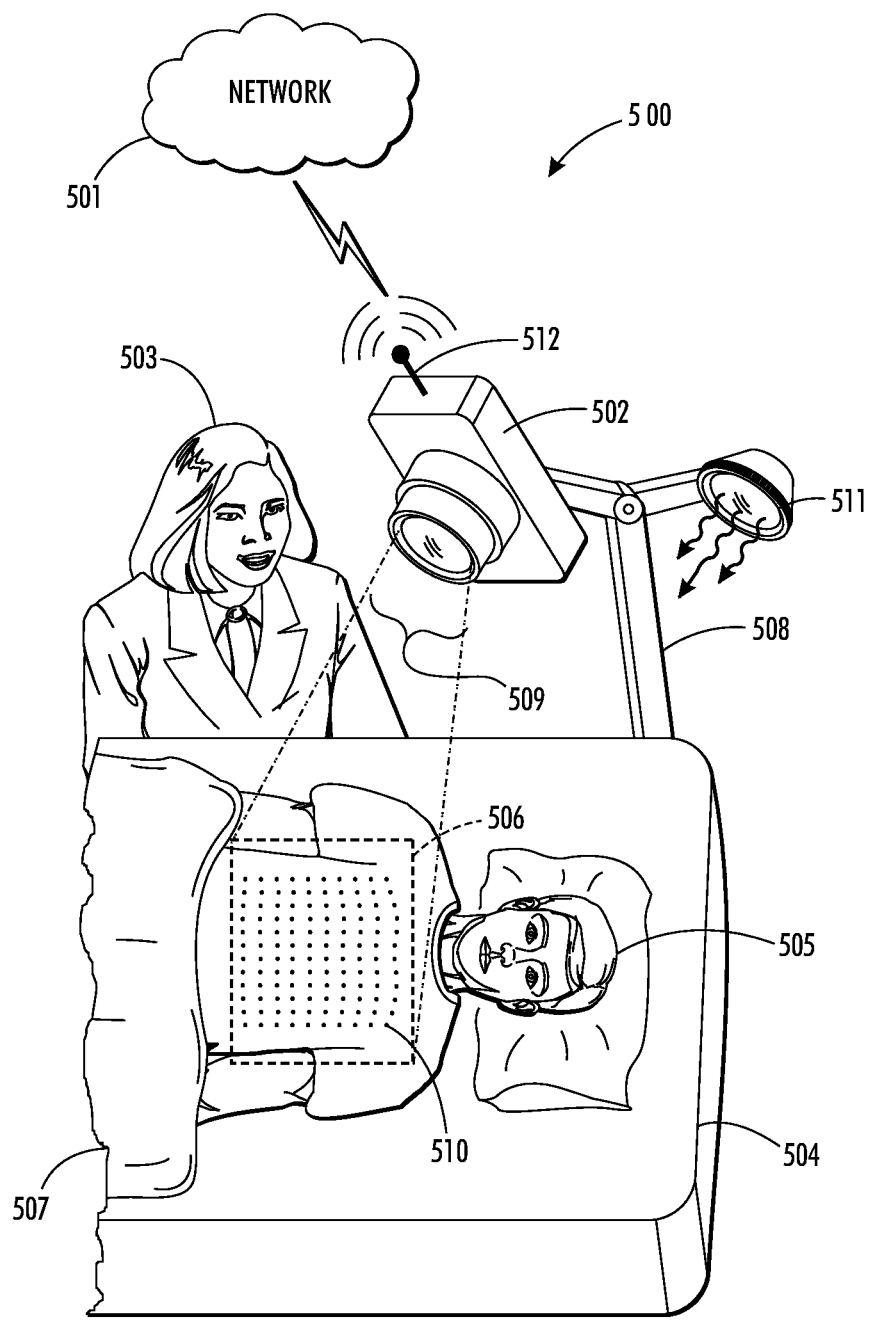
FIG. 5 illustrates one embodiment of an example 2D monocular video camera system acquiring video images of the region of interest of the subject of FIG. 3 being monitored for respiratory function assessment.

Reference is now being made to FIG. 5 which illustrates one embodiment of an example 2D monocular video acquisition system capturing video of a subject of interest of FIG. 3 being monitored for respiratory function assessment.

Examination room 500 has an example 2D monocular video camera system 502 being operated by technician 503 standing at the bedside 504 of subject of interest 505 shown resting his/her head on a pillow while his/her body is partially covered by sheet 507. Patient 505 is wearing a shirt shown with a patterned array of reflective marks, individually at 510. 2D monocular video camera 502 is rotatably fixed to support arm 508 such that the camera's field of view 509 can be directed by the technician onto target region 506 of patient 505 for respiratory function estimation. Support arm 508 is on a set of wheels (not shown) so that video system 502 can be moved from bed to bed and room to room. Although patient 505 is shown in a prone position lying in a bed, it should be appreciated that video of the subject's target region 506 can be captured while the subject is positioned in other supporting devices such as, for example, a chair or in a standing position.

Video camera 502 comprises imaging sensors arrayed on a detector grid. The sensors of the video camera are at least sensitive to a wavelength of an illumination source 511 being reflected by the reflective marks 510. In another embodiment, subject 505 is wearing a shirt having LEDs. Illumination source 511 may be any light wavelength that is detectable by sensors on the camera's detector array. The illumination sources may be manipulated as needed and may be invisible to the human visual system.

A central processor integral to camera 502 and in communication with a memory (not shown) functions to execute machine readable program instructions which process the video and estimate the desired respiratory function(s) which, in turn, are communicated to a nurse, doctor, or technician via transmission element 512 in the event that the respiratory function assessment of patient 505 falls outside a pre-defined parameter. In other embodiments, camera system 502 outputs an alarm, notice, report, and the like, if a change in any hardware or software of the camera has been detected. Video camera 502 may be placed in communication with one or more other sensors capable of sensing a change of status of patient 505 and issue an alarm or notification in response thereto. Antenna 512 can also communicate the captured video to various remote devices via network 501. Camera system 502 may include both wireless and wired elements and may be connected via other means such as coaxial cable, radio frequency, Bluetooth, or any other manner for communicating data. The camera may further incorporate a network card (not shown). Network 501 receives the transmitted video signals, respiratory function estimations, alarm data, and the like, and wirelessly communicates that information to various devices such as, for instance, a workstation with a display device. Data is transferred in the form of signals which may be, for example, electronic, electromagnetic, optical, light, or other signals. These signals may be communicated to a server which transmits and receives data by means of a wire, cable, fiber optic, phone line, cellular link, RF, satellite, or other medium or communications pathway or protocol. Techniques for placing devices in networked communication are well established. As such, further discussion as to specific networking techniques is omitted herein.

Video Processing

Processing the video means constructing a temporal sequence of 3D surface maps of the patterned target region. For each image frame, a depth map is constructed from an amount of spatial distortion (deformation) that has been determined to have occurred between the patterned marks in the target region over time, relative to the spatial characteristics of a known reference pattern. Point-wise correspondences between each video frame and the reference pattern can be readily established using point descriptors such as SIFT, as disclosed in "*Distinctive Image Features From Scale-Invariant Keypoints*", by David G. Lowe, International Journal of Computer Vision (IJCV), Vol. 60. No. 2, pp. 91-110, (2004) or specifically designed matching process for deformable objects as disclosed in "*Fast Non-Rigid Surface Detection, Registration And Realistic Augmentation*", by Julien Pilet, Vincent Lepetit, and Pascal Fua, International Journal of Computer Vision (IJCV), Vol. 76, No. 2, pp. 109-122, (2008), both of which are incorporated herein in their entirety by reference. Other correspondence methods such as performing local correlation operations between portions of the reference and the acquired pattern can be implemented. Assuming there are no mismatches in the established correspondences, a 3D shape can be established from them. In order to minimize the effect of mismatches in the data, statistical techniques such as RANSAC can be implemented alongside the matching process, as disclosed in "*Random Sample Consensus: A Paradigm For Model Fitting With Applications To Image Analysis And Automated Cartography*", by Martin A. Fischler and Robert C. Bolles, Communications of the ACM, Vol. 24, No. 6, pp. 381-395, (1981), which is also incorporated herein in its entirety by reference. If the shape of the template has been characterized in advance, global (semi-rigid) relationships between local features can also be enforced. Since establishing correspondences on patterns with little texture is difficult, patterns with salient features are preferred. The spatial density of the matching correspondences will determine the spatial resolution of the reconstructed 3D surface map. For example, in the pattern of FIG. 2, a depth map with a resolution of 1 dpi can be constructed, although higher resolution depth maps can be recovered via well-known interpolation methods. In should be appreciated that higher-resolution patterns are preferable. Alternatively, dense correspondences between already existing patterned clothing can be exploited. Once point correspondences have been established between each image frame showing the distorted pattern and that of the undistorted reference pattern, the amount of distortion can be determined in each of the (x,y) direction.

Figure 6:
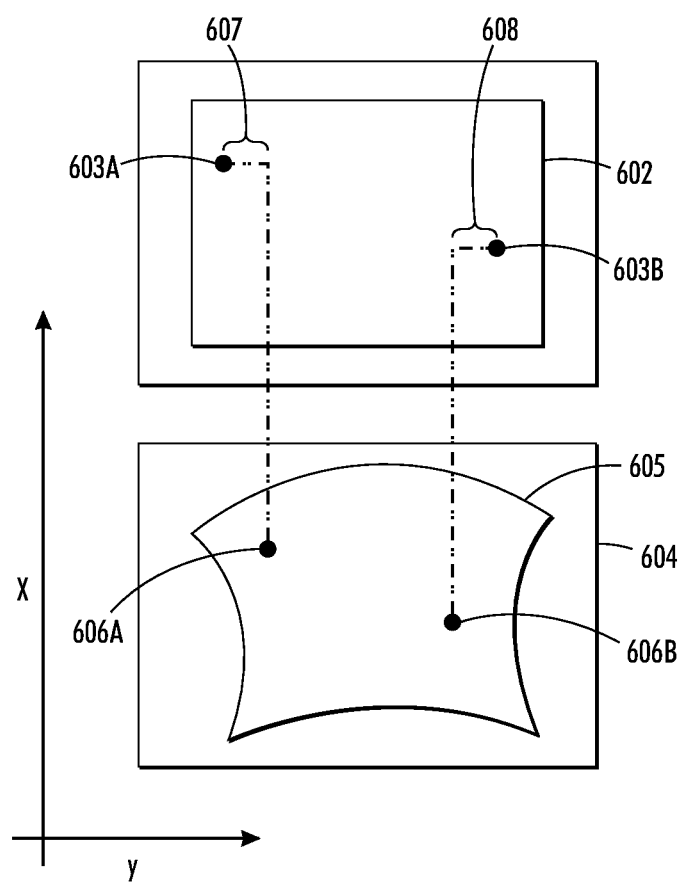
FIG. 6 shows, for explanatory purposes, a point-wise correspondence between an undistorted reference pattern and a distorted pattern over the target region.

Reference is now being made to FIG. 6 which shows an undistorted reference pattern 602 having, for explanatory purposes, only 2 marks thereon (603A-B). Image frame 604 shows a section of shirt 605 having, for explanatory purpose, only 2 marks (606A-B). A point-wise correspondence is established between the reference pattern and each image frame. As shown, the pattern 605 has been distorted by the movement of the subject's rib cage during respiration. These differences are shown at 607 and 608 between respective corresponding marks.

Figure 7:
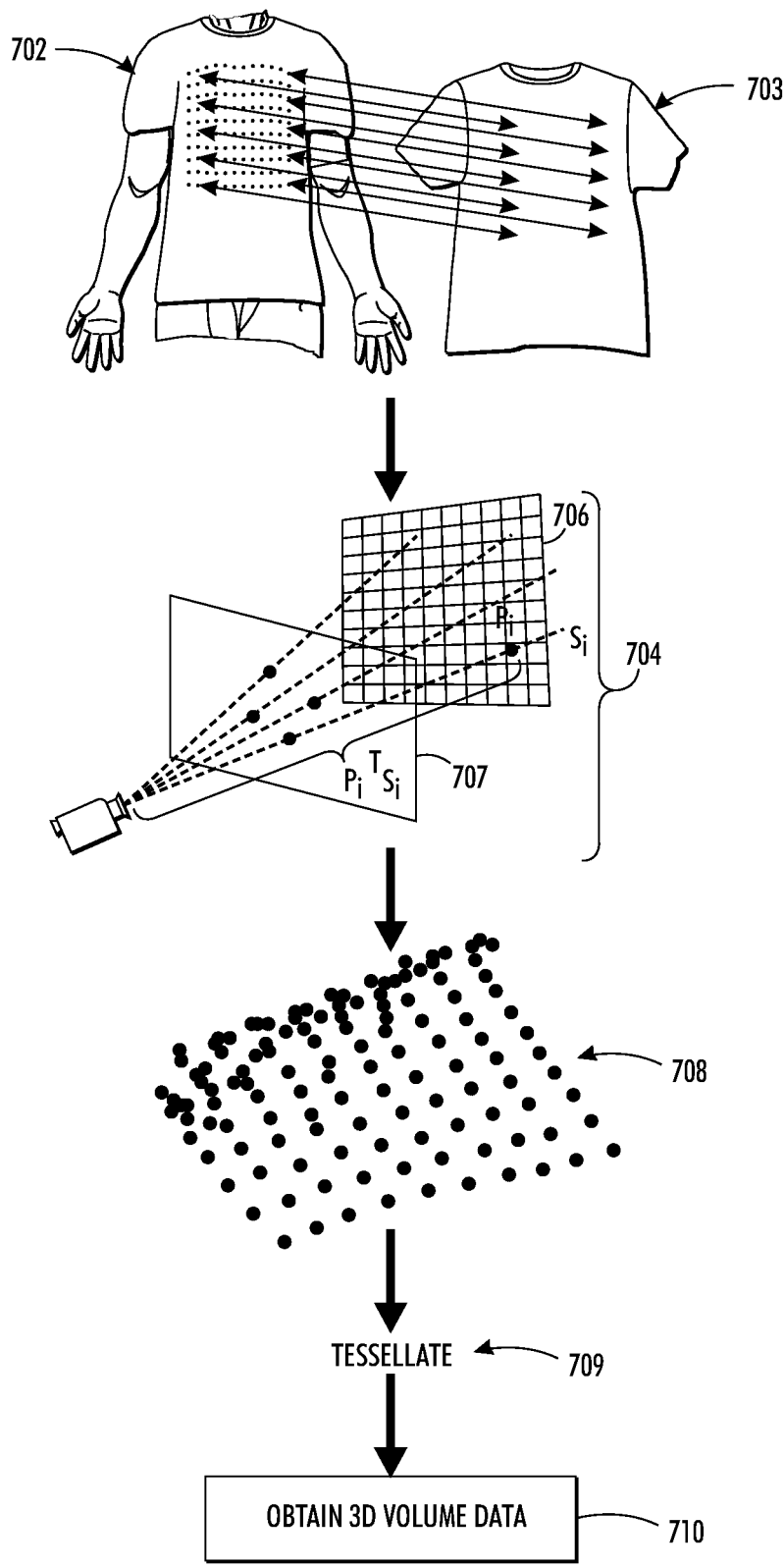
FIG. 7 illustrates the process hereof for determination of depth maps and volume information in accordance with one embodiment of the present method.

Reference is now being made to FIG. 7 which generally illustrates the determination of depth maps and 3D volume information in accordance with the teachings hereof. In FIG. 7, a point-wise correspondence is established, in each image frame, between the distorted pattern 702 and the reference pattern 703. At 704, the camera's 705 internal parameters enable one to compute a back projection 706 of the matched feature points 707 via sightlines. Since the camera is projective, the sightlines intersect at the camera's center and are not parallel to each other, as such the distance between two respective points increases with depth. The template gives the maximal distance between two points so that when the real dimensions of the reference pattern are available, the scale ambiguity can be resolved. This, in turn, is used to compute the depth of matched points such that 3D surface maps for each processed image frame can be reconstructed. The mathematical derivation of this depth computation will next be discussed.

Depth Map Computation

Assuming the internal camera parameters are known, the perspective projection of a 3D point located at spatial coordinates $q_i$ as expressed in camera coordinates is $$d_i \begin{bmatrix} u_i \\ v_i \\ 1 \end{bmatrix} = A q_i$$

where A is the matrix of camera internal parameters, and $d_i$ is a scalar that relays depth information.

If $q_i$ lies on the facet of a triangulated mesh, it can be expressed in barycentric coordinates ($a_i$, $b_i$, $c_i$) as a weighted sum of the facet vertices $v_1$, $v_2$ and $v_3$:

$$d_i \begin{bmatrix} u_i \\ v_i \\ 1 \end{bmatrix} = A(a_i v_1 + b_i v_2 + c_i v_3)$$

If a list of N correspondences for points lying inside one facet, the coordinates of its three vertices $v_1$, $v_2$ and $v_3$ can be computed by solving the following linear system:

$$\begin{bmatrix} a_1 A & b_1 A & c_1 A & -\begin{bmatrix} u_1 \\ v_1 \\ 1 \end{bmatrix} \\ \vdots & \vdots & \vdots & \vdots \\ a_N A & b_N A & c_N A & -\begin{bmatrix} u_N \\ v_N \\ 1 \end{bmatrix} \end{bmatrix} \begin{bmatrix} v_1 \\ v_2 \\ v_3 \\ d_i \end{bmatrix} = 0$$

Since a mesh typically comprises multiple facets or triangles, an overall system of equations is obtained by stacking the individual mesh equations as follows:

$$\begin{bmatrix} a_1 A & b_1 A & c_1 A & 0 & \ldots & \ldots & -\begin{bmatrix} u_1 \\ v_1 \\ 1 \end{bmatrix} & 0 & \ldots & \ldots & \ldots \\ \ldots & \ldots & \ldots & \ldots & \ldots & \ldots & \ldots & \ldots & \ldots & \ldots \\ 0 & b_j A & c_j A & d_j A & 0 & \ldots & 0 & -\begin{bmatrix} u_j \\ v_j \\ 1 \end{bmatrix} & 0 & \ldots & \ldots \\ \ldots & \ldots & \ldots & \ldots & \ldots & \ldots & \ldots & \ldots & \ldots & \ldots \\ a_l A & 0 & c_l A & 0 & e_l A & \ldots & 0 & \ldots & -\begin{bmatrix} u_l \\ v_l \\ 1 \end{bmatrix} & 0 & \ldots \\ \ldots & \ldots & \ldots & \ldots & \ldots & \ldots & \ldots & \ldots & \ldots & \ldots \end{bmatrix} \begin{bmatrix} v_1 \\ \vdots \\ v_{N_v} \\ d_1 \\ \vdots \\ d_{N_c} \end{bmatrix} = 0$$

where $N_f$ denotes the number of facets in the mesh, $N_v$ denotes the number of facet vertices and $N_c$ denotes the number of point correspondences. The leftmost matrix in the above expression has at most full rank minus one, which is related to the scale ambiguity that arises from projecting a 3D scene into a 2D image. In practice, however, it should be treated as a matrix of even lower rank, thus the need to introduce additional constraints to the system. Typically, constant length, shading, illumination and temporal consistency constraints are introduced. Effectively, solving the above system of equations under a set of constraints, allows for reconstruction of the 3D shape of the surface describing the deformed shape of the reference (typically flat) template. We refer to this as a depth map.

Volume Estimation

Depth points (one shown at 708) are obtained. Since the depth map comprises the 3D hull defined by the set of 3D coordinates of the matched points, namely their horizontal, vertical and depth coordinates (x, y and z respectively), a 3D depth map can be obtained by tessellating (at 709) the space bounded by the matched points by, for example, first computing a triangular tessellation of the surface points of the depth maps where the vertices of the triangles are the estimated locations of the 3D points. By definition of a tessellation, the triangles fill the whole surface and do not overlap. Every 3D point is a vertex of at least a triangle in the tessellation. In addition to a surface tessellation, an anchor point located on the back plane of the depth map, and at the algebraic mean of the x and y spatial coordinates of the object's surface is computed. This anchor point defines a hull whose volume can be computed. Since one such volume is available for every frame in the video, the concatenation of all the 3D volumes forms a temporal sequence of volumes which is, in effect, the respiration signal derived from the video. The respiratory signal can be de-trended to remove low frequency variations and a Fast Fourier Transform (FFT) performed. An amplitude of the de-trended signal identifies volume (at 710). A peak detection algorithm applied to the signal identifies frequency components which, in turn, identify respiration rate.

Calibration

The described volume estimation procedure yields uncalibrated volume data, that is, volume data that may not be in standard volumetric units such as liters or cubic meters. While known camera calibration techniques can be applied to obtained calibrated volume data, i.e. to convert pixel values to standard length units such as meters or inches, the estimated volumes reflect the volumetric changes of the area of interest as it expands and contracts with the breathing process. These changes in volume are thus a manifestation of the gas flow associated with respiration, but do not directly correspond to gas volumes, thus an additional calibration step relating calibrated region of interest volumes to gas flow volumes would be required. A simpler one-step approach to calibrating the obtained volumetric data consists in measuring respiratory volumes with a spirometer or a similar instrument while at the same time estimating uncalibrated respiratory volumes according to the teachings herein, and then determine a regression function that relates the uncalibrated estimated volumes to spirometer readouts.

In environments where the patient is free to move around while being monitored for respiratory function, it may become necessary to build pose-dependent calibration functions. Specifically, video or image capture from different points of view is performed, and perspective-dependent respiratory volumes are computed; at the same time, respiratory volumes are measured with a spirometer. Processing of video from each point of view will lead to perspective-dependent or pose-dependent volume estimation, from which multiple calibration tables are built. Calibration for poses and perspectives intermediate to those tested can be accomplished via interpolation functions.

Flow Diagram of One Example Embodiment

Figure 8:
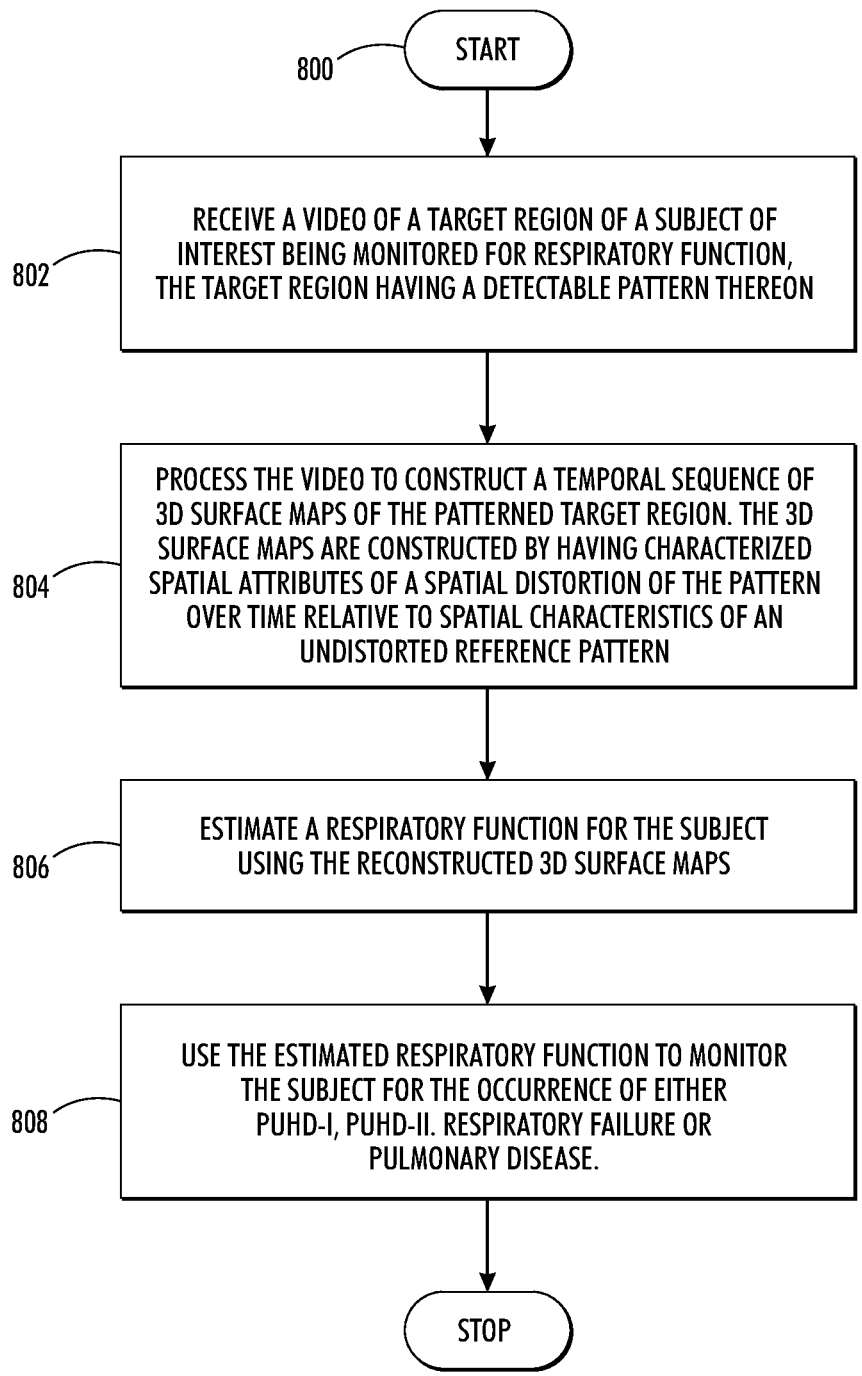
FIG. 8 is a flow diagram which illustrates one example embodiment of the present method for image-based estimation of a respiratory function from a video of a subject of interest captured using a 2D monocular video acquisition system.

Reference is now being made to the flow diagram of FIG. 8 which illustrates one example embodiment of the present method for image-based estimation of a respiratory function from a video of a subject of interest acquired using a 2D monocular video camera. Flow processing begins at step 800 and immediately proceeds to step 802.

At step 802, receiving a video of a target region having a detectable pattern thereon of a subject of interest being monitored for respiratory function assessment. An example target region containing a detectable pattern is shown and discussed with respect to FIGS. 2 and 3. The video has been acquired using a 2D monocular video system shown by way of example in FIG. 5.

At step 804, process the video to construct a temporal sequence of 3D surface maps of the patterned target region. The 3D surface maps are reconstructed by characterizing spatial attributes of a spatial distortion of the pattern over time relative to spatial characteristics of an undistorted reference pattern. Methods for processing the video to obtain 3D surface maps are discussed with respect to FIGS. 6 and 7.

At step 806, estimate a respiratory function for the subject using the 3D surface maps. In various embodiments hereof, the respiratory function comprises any of: tidal chest volume, minute ventilation, respiration rate, inspiratory reserve volume, expiratory reserve volume, residual volume, vital capacity, inspiratory capacity, and functional residual capacity.

At step 808, use the estimated respiratory function to monitor for an occurrence of any of: PUHD-I, PUHD-II, SIDS, Respiratory Failure, and Pulmonary Disease. Thereafter, in this embodiment, further processing stops.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Functional Block Diagram

Figure 9:
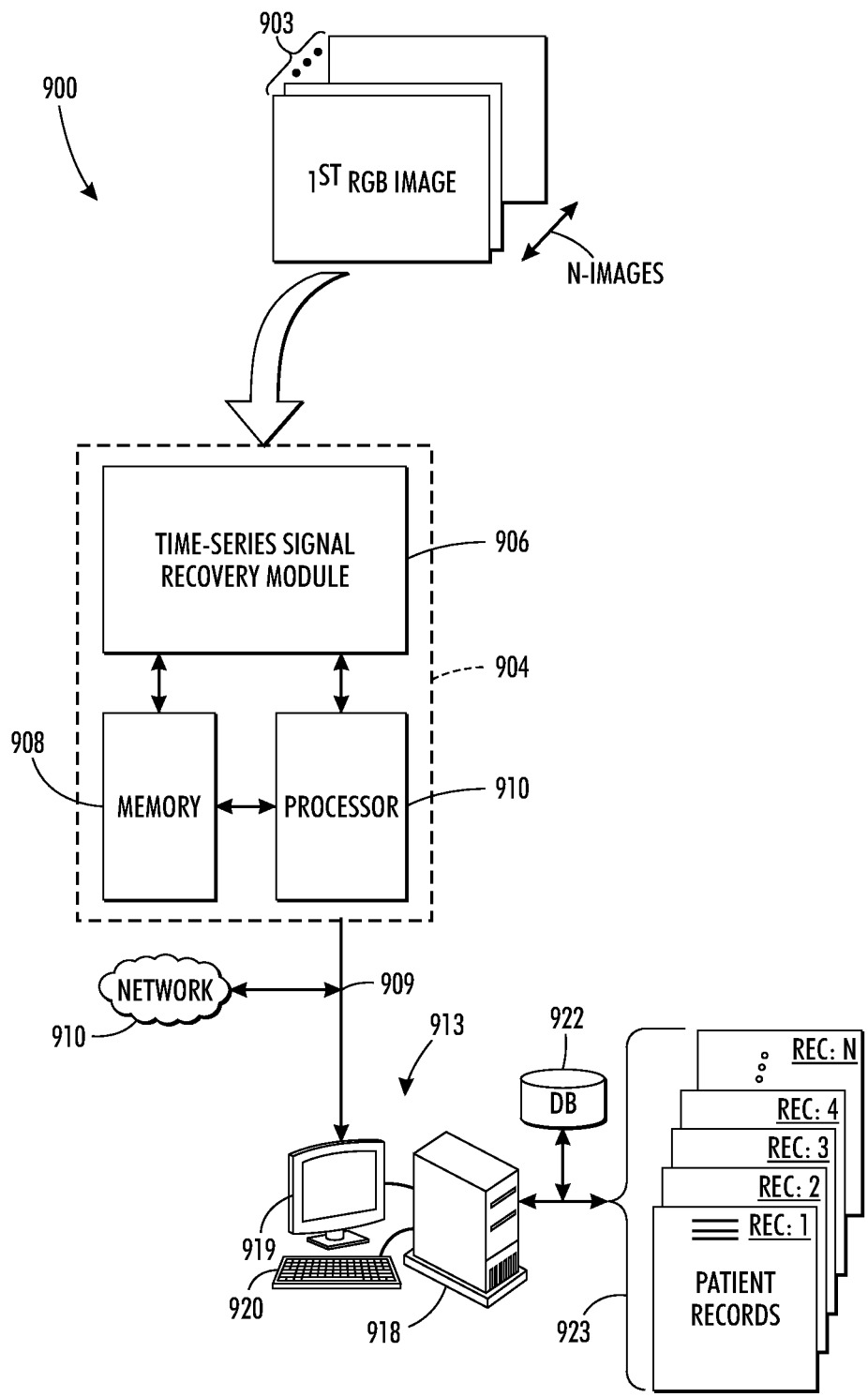
FIG. 9 which illustrates a block diagram of one example processing system 900 capable of implementing various aspects of the present method described with respect to the flow diagram of FIG. 8.

Reference is now being made to FIG. 9 which illustrates a block diagram of one example processing system 900 capable of implementing various aspects of the present method described with respect to the flow diagram of FIG. 8.

The embodiment of FIG. 9 receives a video comprising 2D monocular video images captured of a subject of interest intended to be monitored for respiratory function assessment. The captured video images are a plurality of image frames 902 captured using, for example, the video camera 502 of FIG. 5. The sequence of images 903 collectively comprises source video data acquired over time. Signal processing system 904 receives the video images into time-series signal recovery module 906 which processes the video images, in accordance with the teachings hereof, to obtain a respiratory signal 909. Memory 908 and CPU 910 facilitate processing. Signal 909 is communicated to workstation 913. The respiratory signal 909 may further be communicated to remote devices over network 910. Many aspects of network 910 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway.

Workstation 913 is shown comprising a computer case 918 housing a motherboard, CPU, memory, interface, storage device, and a communications link such as a network card. The computer workstation is also shown having a display device 919 such as a CRT, LCD, or touchscreen display whereon various aspects of the patient's respiratory function are displayed for a technician, nurse, or medical practitioner. Alphanumeric keyboard 920 and a mouse (not shown) effectuate a user input. In the embodiment of FIG. 9, computer system 713 implements database 922 wherein various patient records are stored, manipulated, and retrieved in response to a query. Such records, in various embodiments, take the form of patient medical history wherein the obtained estimated respiratory functions are stored in association with information identifying the subject of interest from which the signals were obtained. Also stored with the patient records (collectively at 923) is information regarding the pattern used, region of interest, camera details, depth maps, 3D surface volumes, and the like. Also stored are mathematical representations and data values used to obtain or otherwise derive the patient's respiratory function estimations. Although the database is shown as an external device, the database may be internal to computer case 918 mounted on a hard disk housed therein. A record refers to any data structure capable of containing information which can be indexed, stored, searched, and retrieved in response to a query. It should be appreciated that patient medical history information can be stored and/or retrieved to any of the records in database 922. It should also be appreciated that the workstation has an operating system and other specialized software configured to display a variety of numeric values, text, scroll bars, pull-down menus with user selectable options, and the like, for entering, selecting, or modifying information displayed on the display device.

A user of the workstation of FIG. 9 may use the graphical user interface to identify or otherwise select candidate image frames or image sub-sections for processing or re-processing. Some or all of the received video may be played by an operator of workstation and viewed on the display, as needed, to facilitate the analysis intended to be performed such that the subject's respiratory function can be monitored. Such facilitation may take the form of the operator selecting one or more frames of the video for viewing, analysis and/or processing. The operator may further direct certain video frames or portions of the received video signals to certain modules and/or processors of the video analysis system of FIG. 9, as needed or desired. The generated respiratory function result(s) may be reviewed by the user or technician. The operator may modify the results as needed and re-direct the modified results back to the same or different modules for further processing or re-processing.

It should be appreciated that the workstation has an operating system and other specialized software configured to display a variety of numeric values, text, scroll bars, pull-down menus with user selectable options, and the like, for entering, selecting, or modifying information displayed on the display device. Upon viewing the determined respiratory function estimations and results, the user may select one or more alternative areas of the target region and provide those to other modules for processing or re-processing. In other embodiments, the generated results are provided directly to a server over network 910 and communicated to a user/operator such as, a physician, nurse, technician, respiratory specialist, to name a few.

Any of the modules and processing units of FIG. 9 are in communication with workstation 913 via pathways (not shown) and may further be in communication with one or more remote devices over network 910. It should be appreciated that some or all of the functionality for any of the modules of system 904 may be performed, in whole or in part, by components internal to workstation 913 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through network 910.

Various Embodiments

It will be appreciated that the above-disclosed and other features and functions, or alternatives thereof, may be desirably combined into many other different systems or applications.

The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be included as part of an operating system, a plug-in, or may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications are each separately hereby incorporated by reference in their entirety.

What is claimed is:

1. A method for processing a video acquired using a 2D monocular video acquisition system to assess respiratory function of a subject of interest in a remote sensing environment, the method comprising:

receiving a video of a target region of a subject of interest being monitored for respiratory function assessment, said video having been acquired using a 2D monocular video acquisition system, said target region having a detectable pattern thereon, said pattern being one of: reflective and emissive in a given wavelength, said wavelength being detectable by sensor elements in a detector array of said camera during acquisition of said video;

processing said video to construct a temporal sequence of 3D surface maps of said patterned target region, said 3D surface maps being reconstructed by characterizing spatial attributes of a spatial distortion of said pattern over time relative to spatial characteristics of an undistorted reference pattern;

estimating time-series data from said temporal sequence of 3D surface maps, comprising:

for each image of said received video:

comparing said characterized spatial attributes of said pattern to known spatial attributes of said undistorted reference pattern to determine an amount of spatial distortion that has occurred locally at different locations on a surface of said patterned target region;

calculating a depth map from said determined amount of spatial distortion;

estimating a volume from said depth map; and concatenating said estimated volumes to obtain said time-series data; and estimating a respiratory function for said subject from said time-series data.

2. The method of claim 1, wherein said target region comprises one of: said subject's anterior thoracic region, a region of said subject's dorsal body, and a side view containing said subject's thoracic region.

3. The method of claim 1, wherein said undistorted reference pattern is virtual.

4. The method of claim 1, wherein said respiratory function comprises any of: tidal chest volume, minute ventilation, respiration rate, inspiratory reserve volume, expiratory reserve volume, residual volume, vital capacity, inspiratory capacity, and functional residual capacity.

5. The method of claim 1, further comprising:

de-trending said time-series data to remove low frequency variations;

performing a Fast Fourier Transform on said de-trended time-series data; and performing peak detection to identify frequency components of said respiratory function over time.

6. The method of claim 1, wherein said detectable pattern comprises any of: salient textural characteristics on said target region, salient textural characteristics of a clothing worn over said target region, a physical characteristic inherent to a surface of said target region, a physical characteristic imprinted on a surface of said target region, and a plurality of emissive sources on said target region at different locations.

7. The method of claim 1, wherein said detectable pattern comprises any of: a pattern of marks on said target region, and a pattern of marks on clothing worn over said target region, said marks being any of: reflective and emissive.

8. The method of claim 1, further comprising using said estimated respiratory function to monitor for an occurrence of any of: PUHD-I, PUHD-II, SIDS, Respiratory Failure, and Pulmonary Disease.

9. A system for processing a video acquired using a 2D monocular video camera system to assess respiratory function of a subject of interest in a remote sensing environment, the system comprising:
a memory and a storage device;
a processor in communication with said memory and storage device, and said 2D monocular video camera, said processor executing machine readable instructions for performing:
receiving a video of a target region of a subject of interest being monitored for respiratory function assessment, said video having been acquired using a 2D monocular video system, said target region having a detectable pattern thereon, said pattern being one of: reflective and emissive in a given wavelength, said wavelength being detectable by sensor elements in a detector array of said camera during acquisition of said video;
processing said video to construct a temporal sequence of 3D surface maps of said patterned target region, said 3D surface maps being reconstructed by characterizing spatial attributes of a spatial distortion of said pattern over time relative to spatial characteristics of an undistorted reference pattern;
estimating time-series data from said temporal sequence of 3D surface maps, comprising:
for each image of said received video:
comparing said characterized spatial attributes of said pattern to known spatial attributes of said undistorted reference pattern to determine an amount of spatial distortion that has occurred locally at different locations on a surface of said patterned target region;
calculating a depth map from said determined amount of spatial distortion;
estimating a volume from said depth map; and
concatenating said estimated volumes to obtain said time-series data;
estimating a respiratory function for said subject from said time-series data; and
communicating said estimated respiratory function to said storage device.

10. The system of claim 9, wherein said target region comprises one of: said subject's anterior thoracic region, a region of said subject's dorsal body, and a side view containing said subject's thoracic region.

11. The system of claim 9, wherein said undistorted reference pattern is virtual.

12. The system of claim 9, wherein said respiratory function comprises any of: tidal chest volume, minute ventilation, respiration rate, inspiratory reserve volume, expiratory reserve volume, residual volume, vital capacity, inspiratory capacity, and functional residual capacity.

13. The system of claim 9, further comprising:
de-trending said time-series data to remove low frequency variations;
performing a Fast Fourier Transform on said de-trended time-series data; and
performing peak detection to identify frequency components of said respiratory function over time.

14. The system of claim 9, wherein said detectable pattern comprises any of: salient textural characteristics on said target region, salient textural characteristics of a clothing worn over said target region, a physical characteristic inherent to a surface of said target region, a physical characteristic imprinted on a surface of said target region, and a plurality of emissive sources on said target region at different locations.

15. The system of claim 9, wherein said detectable pattern comprises any of: a pattern of marks on said target region, and a pattern of marks on clothing worn over said target region, said marks being any of: reflective and emissive.

16. The system of claim 9, further comprising using said estimated respiratory function to monitor for an occurrence of any of: PUHD-I, PUHD-II, SIDS, Respiratory Failure, and Pulmonary Disease.

17. A method for processing an image acquired using a 2D monocular video acquisition system to assess a respiratory function of a subject of interest in a remote sensing environment, the method comprising:
receiving an image of a target region of a subject of interest being monitored for respiratory function assessment, said image having been acquired using a 2D monocular video acquisition system, said target region having a detectable pattern thereon, said pattern being one of: reflective and emissive in a given wavelength, said wavelength being detectable by sensor elements in a detector array of said camera during acquisition of said video;
processing said image to obtain a 3D surface map of said patterned target region, said 3D surface map being reconstructed by characterizing spatial attributes of a spatial distortion of said pattern relative to spatial characteristics of an undistorted reference pattern;
estimating time-series data from said 3D surface map, comprising:
for each image of said received video:
comparing said characterized spatial attributes of said pattern to known spatial attributes of said undistorted reference pattern to determine an amount of spatial distortion that has occurred locally at different locations on a surface of said patterned target region;
calculating a depth map from said determined amount of spatial distortion;
estimating a volume from said depth map; and
concatenating said estimated volumes to obtain said time-series data; and
assessing a respiratory function for said subject from said time-series data.

18. The method of claim 17, wherein said target region comprises one of: said subject's anterior thoracic region, a region of said subject's dorsal body, and a side view containing said subject's thoracic region.

19. The method of claim 17, wherein said undistorted reference pattern is virtual.

20. The method of claim 17, wherein said detectable pattern comprises any of: salient textural characteristics on said target region, salient textural characteristics of a clothing worn over said target region, a physical characteristic inherent to a surface of said target region, a physical characteristic imprinted on a surface of said target region, and a plurality of emissive sources on said target region at different locations.

21. The method of claim 17, wherein said detectable pattern comprises any of: a pattern of marks on said target region, and a pattern of marks on clothing worn over said target region, said marks being any of: reflective and emissive.

* * * * *